United States Patent [19]

Randell et al.

[11] 3,939,170

[45] Feb. 17, 1976

[54] DEHYDRO PYRIDINYL SULFIDES, SULFOXIDES AND SULFONES

[75] Inventors: Donald Richard Randell, Stockport; Malcolm John Smith, Marple Stockport, both of England

[73] Assignee: Ciba-Geigy Corporation, Ardsley, N.Y.

[22] Filed: June 3, 1974

[21] Appl. No.: 475,717

[30] Foreign Application Priority Data

June 8, 1973 United Kingdom............... 27354/73

[52] U.S. Cl. ...... 260/294.8 F; 260/45.8 R; 260/814; 260/294.8 G
[51] Int. Cl.². .................................. C07D 211/70
[58] Field of Search ............... 260/294.8 F, 294.8 G

[56] References Cited
UNITED STATES PATENTS 2,870,163  1/1959  Davis et al.................... 260/294.8 F

*Primary Examiner*—Henry H. Jiles
*Assistant Examiner*—R. W. Ramsuer
*Attorney, Agent, or Firm*—Nestor W. Shust

[57] ABSTRACT

Compounds having the formula

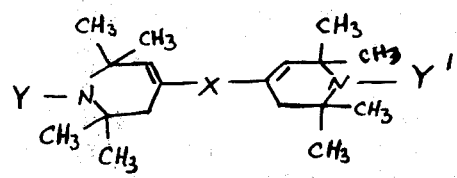

where X is S, SO or $SO_2$ and Y and $Y^1$ are the same or different and each is H, OH, O· or a straight- or branched alkyl residue having from 1 to 4 carbon atoms, and salts thereof when Y and $Y^1$ are other than O· are useful as stabilisers for organic materials such as diene rubbers.

10 Claims, No Drawings

DEHYDRO PYRIDINYL SULFIDES, SULFOXIDES AND SULFONES

The present invention relates to new piperidine derivatives and in particular to new di-4-(3,4-dehydro-2,2,6,6-tetramethylpiperidinyl) sulphides, sulphoxides and sulphones useful as stabilisers for organic materials.

According to the present invention, there are provided compounds having the formula:-

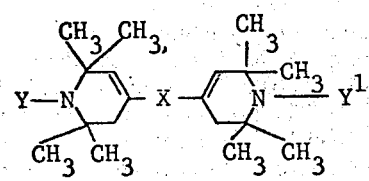 I wherein X is S, SO or $SO_2$ and Y and $Y^1$ are the same or different and each is H, OH, 0° or a straight- or branched alkyl residue having from 1 to 4 carbon atoms, and salts thereof when Y and $Y^1$ are other than 0°.

Preferably X is S.

Examples of alkyl substituents Y and $Y^1$ include methyl, ethyl, n-propyl, isopropyl, n-butyl and secbutyl residues. Particularly preferred substituents Y and $Y^1$ are hydrogen and methyl residues.

Salts of compounds of formula I where Y and $Y^1$ are other than 0° include those formed from the amine functions with inorganic or organic acids, for instance hydrogen chloride, sulphuric acid, phosphoric acid, carbonic acid, acetic acid, maleic acid, malic acid, oxalic acid and tartaric acid.

Specific examples of compounds of formula I are:
Where X is S:

Di-4-(3,4-dehydro-2,2,6,6-tetramethylpiperidinyl) sulphide
Di-4-(3,4-dehydro-1,2,2,6,6-pentamethylpiperidinyl) sulphide
Di-4-(3,4-dehydro-1-ethyl-2,2,6,6-tetramethylpiperidinyl) sulphide
Di-4-(3,4-dehydro-1-isopropyl-2,2,6,6-tetramethylpiperidinyl) sulphide
Di-4-(3,4-dehydro-1-n-butyl-2,2,6,6-tetramethylpiperidinyl) sulphide
4-(3,4-dehydro-2,2,6,6-tetramethylpiperidinyl) 4'-(3',4'-dehydro-1',2',2',6',6'-pentamethylpiperidinyl) sulphide
4-(3,4-dehydro-1,2,2,6,6-pentamethylpiperidinyl) 4'-(1'-butyl-3',4'-dehydro-2',2',6',6'-tetramethylpiperidinyl) sulphide
4-(3,4-dehydro-2,2,6,6-tetramethylpiperidinyl) 4'-(3',4'-dehydro-1'-hydroxy-2',2',6',6'-tetramethyl piperidinyl) sulphide
Di-4-(3,4-dehydro-1-oxy-2,2,6,6-tetramethylpiperidinyl) sulphide
4-(3,4-dehydro-2,2,6,6-tetramethylpiperidinyl) 4'-(3',4'-dehydro-1'-oxy-2',2',6',6'-tetramethylpiperidinyl) sulphide
4-(1-butyl-3,4-dehydro-2,2,6,6-tetramethylpiperidinyl) 4'-(3',4'-dehydro-1'-oxy-2',2',6',6'-tetramethylpiperidinyl) sulphide
Di-4-(3,4-dehydro-2,2,6,6-tetramethylpiperidinyl) sulphide dihydrochloride Where X is SO:

Di-4-(3,4-dehydro-2,2,6,6-tetramethylpiperidinyl) sulphoxide
Di-4-(3,4-dehydro-1,2,2,6,6-pentamethylpiperidinyl) sulphoxide
Di4-(3,4-dehydro-1-ethyl-2,2,6,6-tetramethylpiperidinyl) sulphoxide
Di-4-(3,4-dehydro-1isopropyl-2,2,6,6-tetramethylpiperidinyl) sulphoxide
Di-4-(3,4-dehydro-1-n-butyl-2,2,6,6-tetramethylpiperidinyl) sulphoxide
4-(3,4-dehydro-1,2,2,6,6-pentamethylpiperidinyl) 4'-(1'-ethyl-3',4'-dehydro-2',2',6',6'-tetramethylpiperidinyl) sulphoxide
4-(3,4-dehydro-1,2,2,6,6-pentamethylpiperidinyl) 4'-(1'-butyl-3',4'-dehydro-2',2', 6', 6'-tetramethylpiperidinyl) sulphoxide
4-(3,4-dehydro-2,2,6,6-tetramethylpiperidinyl) 4'-(3',4'-dehydro-1'-hydroxy-2',2',6',6'-tetramethylpiperidinyl) sulphoxide
Di-4-(3,4-dehydro-1-oxy-2,2,6,6-tetramethylpiperidinyl) sulphoxide
4-(3,4-dehydro-1-n-propyl-2,2,6,6-tetramethylpiperidinyl) 4'-(3',4'-dehydro-1'-oxy-2',2',6',6'-tetramethylpiperidinyl sulphoxide
4-(1-butyl-3,4-dehydro-2,2,6,6-tetramethylpiperidinyl) 4'-(3',4'-dehydro-1'-oxy-2',2',6',6'-tetramethylpiperidinyl) sulphoxide
Di-4-(3,4-dehydro-1,2,2,6,6-pentamethylpiperidinyl) sulphoxide dihydrobromide Where X is $SO_2$:

Di-4-(3,4-dehydro-2,2,6,6-tetramethylpiperidinyl) sulphone
Di-4-(3,4-dehydro-1,2,2,6,6-pentamethylpiperidinyl) sulphone
Di-4-(3,4-dehydro-1ethyl-2,2,6,6-tetramethylpiperidinyl) sulphone
Di-4-(3,4-dehydro-1-isopropyl-2,2,6,6-tetramethylpiperidinyl) sulphone
Di-4-(3,4-dehydro-1-n-butyl-2,2,6,6-tetramethylpiperidinyl) sulphone
4-(3,4-dehydro-1,2,2,6,6-pentamethylpiperidinyl) 4'-(1'-ethyl-3',4'-dehydro-2',2',6',6'-tetramethylpiperidinyl) sulphone
4-(3,4-dehydro-1,2,2,6,6-pentamethylpiperidinyl) 4'-(1'-butyl-3',4'-dehydro-2', 2',6',6'-tetramethylpiperidinyl) sulphone
4-(3,4-dehydro-1,2,2,6,6-pentamethylpiperidinyl) 4'-(3',4'-dehydro-1'-hydroxy-2',2',6',6'-tetramethylpiperidinyl) sulphone
Di-4-(3,4-dehydro-1-oxy-2,2,6,6-tetramethylpiperidinyl) sulphone
4-(3,4-dehydro-2,2,6,6-tetramethylpiperidinyl) 4'-(3',4'-dehydro-1'-oxy-2',2',6',6'-tetramethylpiperidinyl) sulphone
4-(1-butyl-3,4-dehydro-2,2,6,6-tetramethylpiperidinyl) 4'-(3',4'-dehydro-1'oxy-2',2',6',6'-tetramethylpiperidinyl) sulphone
4-(3,4-dehydro-1,2,2,6,6(pentamethylpiperidinyl) 4'-(3',4'-dehydro-2,2,6,6-tetramethylpiperidinyl) sulphone dihydrochloride.

The present invention also provides a process of producing a compound of formula I wherein X is S and Y and $Y^1$ are the same or different and each is H, OH or a straight- or branched alkyl residue having from 1 to 4 carbon atoms, comprising reacting a compound having the formula

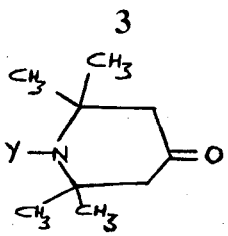

II or an inorganic salt thereof, with a compound of formula

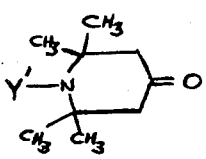

III or an inorganic salt thereof and with a gaseous mixture of hydrogen sulphide and hydrogen chloride.

To produce a symmetrical compound of formula I, compounds of formula II and III in which Y and $Y^1$ are identical are used; whereas to produce an unsymmetrical compound of formula I, compounds of formula II and III are used on which Y and Y' are different from one another. This provides a mixture containing the three possible compounds. The pure compounds may be isolated from the mixture by conventional techniques for instance chromatography.

The reaction may be conveniently carried out in a solvent inert under the reaction conditions, suitable solvents being, for instance, aliphatic alcohols. The reaction temperature employed is preferably within the range of from 0°C. to the reflux temperature of the reaction mixture.

The starting materials of formulas II and III are compounds which are known per se.

The present invention also provides a process of producing a compound of formula I wherein X has its previous significance and Y, $Y^1$ are each an alkyl residue, comprising reacting a compound of formula I wherein X has its previous significance and Y and $Y^1$ are each hydrogen, with an alkylating agent.

Preferably, the alkylating agent is an alkyl halide R-hal wherein R is a straight- or branched alkyl residue having from 1 to 4 carbon atoms and hal, denotes a halogen atom, preferably a chlorine atom.

A compound of formula I wherein X has its previous significance; and Y and $y^1$ are each an alkyl residue, may also be produced by a Leuchart, Wallach or Eschweiler Clarke reaction by reacting a compound of formula I wherein X has its previous significance and Y and $Y^1$ are each H with formic acid and the appropriate aldehyde or ketone. In this way, for instance the N,N'-dimethyl derivative of formula I may be obtained by reacting the compound of formula I, wherein Y and $Y^1$ are each H with formic acid and formaldehyde.

The compound of formula I wherein X has its previous significance and Y,$Y^1$ are each other than 0° may be conveniently isolated from the respective reaction mixtures as their acid salts. The free amines of formula I may then be obtained by treating the salts with the stoichiometric proportion of a base such as sodium carbonate or sodium hydroxide. If desired, the compounds of formula I may be further purified by conventional techniques such as crystallisation from a suitable solvent.

The present invention also provides a process of producing a compound of formula I in which X is SO and Y and $Y^1$ are the same or different and each is H, alkyl or 0°, comprising reacting a compound of formula I in which X is S and Y and $Y^1$ have their previous significance, with an oxidising agent such as hydrogen peroxide or a per-acid. Preferably the oxdation is conducted in an organic acid solvent such as acetic acid. The oxidation is conveniently effected at a temperature within the range of from 0°C. to the reflux temperature of the reaction mixture.

The present invention further provides a process of producing a compound of formula I wherein X is $SO_2$ and Y and $Y^1$ are the same or different and each is H, alkyl or 0°, comprising reacting a compound of formula I in which X is S or SO and Y and $Y^1$ have their previous significance with an oxidising agent such as hydrogen peroxide. Preferably the oxidation is conducted in aqueous or alcoholic solution and in the presence of oxidation catalysts such as tungstic acid, sodium tungstate or benzyl trimethyl ammonium chloride. The oxidation is conveniently effected at a temperature within the range of from 0°C. to the reflux temperature of the reaction mixture.

The present invention further provides a process of producing the compounds of formula I in which X is $SO_2$ and Y and $Y^1$ are each H or alkyl and at least one of Y and $Y^1$ is H, comprising reducing a compound of formula I in which X is $SO_2$ and Y and $Y^1$ are H, 0° or alkyl and at least one of Y and $Y^1$ is 0°. The reduction process may be effected using a hydrogenation technique in a solvent inert under the reaction conditions, for instance an aliphatic alcohol having from 1 to 4 carbon atoms, and in the presence of a hydrogenation catalyst, for instance Raney nickel.

The present invention also provides a process of producing the compounds of formula I in which X is $SO_2$ and Y and $Y^1$ are H, OH or alkyl, at least one of Y and $Y^1$ being OH, comprising reducing a compound of formula I in which X is $SO_2$, and Y and $Y^1$ are H, 0° or alkyl, at least one of Y, and $Y^1$ being 0°. The reduction process may be effected using a hydrogenation technique in a solvent inert under the reaction conditions, for instance an aliphatic alcohol having from 1 to 4 carbon atoms or an aliphatic or cycloaliphatic ether, for instance dioxane, and in the presence of a hydrogenation catalyst, for instance palladium. The catalyst may be used in a pure form or supported upon an inert carrier such as alumina, calcium carbonate or carbon.

The present invention still further provides a a process of producing the compounds of formula I in which X is S and Y and $Y^1$ are H, OH or alkyl comprising reducing a compound of formula I in which X is SO and Y and $Y^1$ have their previous significance. The reduction process may be effected by any suitable reducing agent, for instance lithium aluminium hydride or a mixture of zinc and acetic acid.

The compounds of formula I have been found to be useful as stabilisers for organic materials and are especially effective as stabilisers against the actions of oxygen and ozone in hydrocarbon polymers, and are particularly useful as antiozonants for natural and synthetic rubbers, such as crosslinked, cured or vulcanized rubbers.

The compounds of formula I, especially those compounds in which Y and $Y^1$ are other than 0°, have the added advantage that they do not dicolour rubber into which they are incorporated as stabilisers.

Accordingly, the present invention also provides a composition comprising an organic material and, as stabiliser, a minor proportion of a compound of formula I as hereinbefore defined.

The amount of the compound of formula I which is incorporated into the organic material in order to achieve maximal protection against oxidative degradation varies according to the properties of the organic material treated. However, for most purposes it is sufficient to use an amount of the compound of formula I within the range of from 0.01 to 5% by weight based on the weight of untreated organic material.

The compounds of formula I may be incorporated into the polymeric material by any of the known techniques for compounding additives with a polymer. For example, the compound of formula I, the other polymer additives and the polymer may be compounded in an internal mixer or on a two roll mill.

Organic materials susceptible to oxidative degradation and the properties of which are improved by the incorporation therein of a compound of formula I include natural and synthetic polymeric materials, for instance natural and synthetic rubbers, the latter including: styrene butadiene rubber, polyisoprene rubber, polybutadiene rubber, isobutene-isoprene rubber, epichlorhydrin rubbers, ethylene-propylene rubber, ethylene-propylene diene rubber, propylene oxide rubber, chloroprene rubber, nitrile chloroprene rubber, acrylonitrile butadiene rubber, polyacrylic rubber, silicone rubber, fluorocarbon rubber, fluorosilicone rubber, thiokol rubber, polyurethane rubber, chlorosulphonated polyethylene rubber, reclaimed rubber of any type or any blends in any proportion.

Those may optionally be combined with a filler consisting of, for instance, a. a carbon black, a furnace or channel black or any carbon black of other type or, b. a filler other than carbon black of an inorganic nature such as: aluminum hydroxide, aluminium silicate, ammonium carbonate, antimony sulphide, antimony trioxide, asbestos, barium ferrite, barium sulphate (barytes), barium sulphate (blanc-fixe), barium sulphate/zinc sulphide mixtures, calcium carbonate, calcium oxide (hydrated), calcium silicate, calcium sulphate, china clays, french chalk or talc, graphite, ground glass, hydrated silicas, kieselguhr, litharge, magnesium carbonate, magnesium oxide, metal powders, mica, pumice, silica, titanium dioxide (anatase or rutile), whiting (ground or precipitated), zinc carbonate, zinc oxide, zinc sulphide or any other filler of this type, or c. a filler other than described in (a) and (b) above of an organic nature such as: flocks or organic fibres, such as cotton, rayon, wool, nylon etc., woodflour, coal dust, cork, animal glue, reclaimed rubber, chemically modified natural rubber, synthetic resins of polymeric materials other than rubber or any other filler of this type, or d. a filler other than described in (a), (b) and (c) above of an inorganic or organic nature used mainly for imparting a desired colour to the rubber mixture such as: cadmium sulphide, cadmium sulphoselenide, chromium oxide, iron oxide, lead chromate, mercuric sulphide, nickel titanate, phthalocyanine pigments, quinacridone pigments, ultramarine blue, or any other pigmenting or colouring material.

Any of the fillers described may be mixed with each other in any combinations and in any proportions.

These fillers may also be combined with the rubber materials which plasticise, soften, extend rubber formulations or aid processing of such formulations. Among those are: petroleum oils (paraffinic, naphthenic, aromatic), petroleum jelly, chlorinated paraffinic hydrocarbons, ester platicisers such as dibutyl sebacate, di-isooctyl phthalate, trixylyl phosphate, fatty acids or salts thereof, pine tars, waxes, bitumens, synthetic resins such as coumarone resins, petroleum resins, high styrene/butadiene resins, phenol-formaldehyde resins, thiophenates, thiobenzoic acid salts, organic disulphides, polyester glycols.

Other antidegradants may also be combined with the rubbers for additional protection against the effects of oxygen, heat, flexing, metallic contamination and ozone. These include phenyl α- or β- naphthylamines, ketone-amine condensates, such as acetone-anilines or acetone diphenylamine product mixtures, substituted diphenylamines, substituted phenols, bis phenols, di-p-hydroxyphenylsulphides, mercaptobenzimadazoles, dihydroquinoline derivatives and p-phenylene diamine derivatives such as N, N'-bis(1-ethyl-3-methylpentyl)-p-phenylenediamine, N,N'-bis(1,4-dimethylpentyl)-p-phenylenediamine, N,N'-bis(1-methylheptyl)-p-phenylenediamine, N-isopropyl-N'-phenyl-p-phenylenediamine, N-1,3(dimethylbutyl)-N'-phenyl-p-phenylenediamine, N,N'-diphenyl-p-phenylenediamine and dicyclohexyl-p-phenylenediamine.

Any materials which will cross-link or vulcanise the rubbers may also be added. These may include:

i. sulphur, and/or one or more of the following compounds:

Thiazoles
 Mercaptobenzthiazole (MBT), dibenzthiazyl
 disulphide, sodium salt of MBT.
Sulphenamides
 N-cyclohexylbenzthiazylsulphenamide,
 N-Oxydiethylbenzthiazylsulphenamide.
Dithiocarbamates
 Piperidine pentamethylene dithiocarbamate,
 zinc diethyl dithiocarbamate, sodium
 diethyl dithiocarbamate, zinc ethyl
 phenyl dithiocarbamate.
Thiuram sulphides
 Tetramethyl thiuram disulphide,
 tetraethylthiuram disulphide,
 tetramethylthiuram monosulphide,
 dipentamethylene thiuram tetrasulphide.
Xanthates
 Zinc isopropyl xanthate, sodium isopropyl xanthate, zinc butyl xanthate.
Morpholino disulphides
 Bis-morpholinedisulphide or any materials related to them, and optionally, zinc oxide or stearic acid in any amount for each additive.

ii. sulphur and oxides of zinc, calcium, magnesium and lead or any other metal oxide.

iii. metal oxides or mixtures thereof with or without the addition of an organic accelerator.

iv. quinone dioxime or derivatives thereof.

v. phenol-formaldehyde resins.

vi. organic peroxides such as: benzoyl peroxide, 2,4-dichlorobenzoyl peroxide, or dicumyl peroxide.

vii. polyfunctional amines such as thiourea, 2-mercaptoimidazoline, triethylene tetramine, hexamethylene diamine carbamate, ethylene diamine carbamate, bis-cinnamylidenehexanediamine and bis-p-aminocyclohexylmethane carbamate.

The cross-linking may be carried out at any convenient and effective temperature or pressure.

Any of the rubbers may also be cross-linked, as desired, and where feasible, by high energy radiation with or without the addition of the above-mentioned cross-linking agents.

Some Examples will now be given. Parts and percentages are by weight unless otherwise stated.

EXAMPLE 1

Di-4-(3,4-dehydro-2,2,6,6-tetramethylpiperidinyl) sulphide. 70 Parts by weight of 2,2,6,6-tetramethylpiperidin-4-one hydrochloride were dissolved in the minimum amount of warm ethanol (about 700 parts by volume) and the solution was treated whilst being stirred with hydrogen sulphide and hydrogen chloride gases simultaneously. The rate of addition of the gases was controlled so that the temperature of the reaction did not exceed 70°C. After 5 hours the ethanol was evaporated under reduced pressure and the residue dissolved in water. The solution was basified by the addition of sodium carbonate and then extracted into ether. The ether solution was washed with water, dried over magnesium sulphate (anhydrous) and evaporated under reduced pressure. The solid residue was crystallised from petroleum ether (b.p. 60°-80°C) to yield 28 parts of the product melting at 61°-63°C. and having the following elemental analysis.

$C_{18}H_{32}N_2S$ requires: C, 70.05%; H, 10.45%; N, 9.08%; S, 10.40%. found: C, 69,90%; H, 10.13%; N, 8.71%; S, 10.03%.

EXAMPLE 2

Di-4-(3,4-dehydro-1,2,2,6,6-pentamethylpiperidinyl) sulphide. 5 Parts by weight of di-4-(3,4-dehydro-2,2,6,6-tetramethylpiperidinyl) sulphide was dissolved in 10 parts by weight of formic acid and treated with 3 parts by weight of 37 % formaldehyde solution. The solution was heated on a steam bath for 48 hours, poured into water and basified with sodium carbonate, The mixture was extracted into ether, the organic phase dried over magnesium sulphate (anhydrous) and exporated under reduced pressure. The white solid was crystallised from a methanol-water mixture to yield 3.7 parts of the desired product melting at 79°-82°C. and having the following elemental analysis.

$C_{20}H_{36}N_2S$ requires: C, 71.38%; H, 17 10.78%; N, 8.32%; S, 9.52%. found: C, 71.65%; H, 10.68%; N, 8.36%; S, 9.38%.

EXAMPLE 3

Di-4-(3,4-dehydro-2,2,6,6-tetramethylpiperidinyl) sulphide dihydrochloride. 1 Part by weight of di-4-(3,4-dehydro-2,2,6,6-tetramethylpiperidinyl) sulphide was dissolved in methanol and treated with a 5 % solution of hydrogen chloride in methanol until the resulting solution was acid. The mixture was evaporated under reduced pressure and the residue crystallised from a chloroform-methanol petroleum (b.p. 60°-80°C) mixture to yield the desired product melting at >350°C and having the following elemental analysis.

$C_{18}H_{34}N_2SCl_2$ requires: C, 56.69%; H, 8.98%; N, 7.33%; S, 8.40%; Cl, 18.60%. found: C, 56.35%; H, 8.90%; N, 7.00%; S, 8.34%; Cl, 19.04 %.

EXAMPLE 4

Di-4-(3,4-dehydro-2,2,6,6-tetramethylpiperidinyl) sulphoxide. 3 Parts of di-4-(3,4-dehydro-2,2,6,6-tetramethylpiperidinyl) sulphide was dissolved in 20 parts of 50% aqueous acetic acid and the solution treated with 1.1 parts of 30% hydrogen peroxide solution. This solution was stirred overnight at room temperature and then evaporated. The residue was dissolved in water and basified with excess sodium carbonate. After being washed by shaking with ether the aqueous layer was saturated with sodium chloride and extracted 3 times with chloroform. The chloroform extracts were combined, dried with anhydrous magnesium sulphate and evaporated under reduced pressure. Crystallisation of the residue from petroleum ether (b.p. 80°-100°C.) yielded the desired product melting at 185°-186°C and having the following elemental analysis:

$C_{18}H_{32}N_2SO$ requires: C, 66.63%; H, 9,94%; N, 8.63%; S, 9.86%. found: C, 66.82%; H, 9.90%; N, 8.43%; S, 9.67 %.

EXAMPLE 5

Di-4-(3,4-dehydro-1,2,2,6,6-pentamethylpiperidinyl) sulphoxide. 3 Parts of di-4-(3,4-dehydro-1,2,2,6,6 pentamethylpiperidinyl) sulphide were treated as in Example 4. The residue obtained from the evaporation of the chloroform extracts was crystallised from petroleum ether (b.p. 60°-80°C.) to yield the desired product melting at 128°-131°C. and having the following elemental analysis.

$C_{20}H_{36}N_2SO$ requires: C, 68.14%; H, 10.29%; N, 7.95%; S, 9.08%. found: C, 68.44%; H, 10.22%; N, 7.81%; S, 8.89 %.

EXAMPLE 6

4-(3,4-dehydro-2,2,6,6-tetramethylpiperidinyl) 4'-(3',4'-dehydro-1'-oxy-2',2',6',6'-tetramethylpiperidinyl) sulphone.

1 Part of di-4-(3,4-dehydro-2,2,6,6-tetramethylpiperidinyl) sulphide was dissolved in 20 parts of methanol and 25 parts of water and this treated with 0.1 parts of sodium tungstate and 0.1 part of benzyl trimethyl ammonium chloride. This solution was treated with 4 parts of 30% hydrogen peroxide and stirred for 3 hours. The crystalline precipitate was separated, washed with water and crystallised from a methanol-water mixture to yield the desired product melting at 222°-223°C. and having the following elemental analysis:

$C_{18}H_{31}N_2O_3S$ requires: C, 60.80%; H, 8.79%; N, 7.88%; S, 9.02%. found: C, 60.86%; H, 8.78%; N, 7.84%; S, 9.34 %.

EXAMPLE 7

Di-4-(3,4-dehydro-1,2,2,6,6-pentamethylpiperidinyl) sulphone. 1 Part of di-4-(3,4-dehydro-1,2,2,6,6-pentamethylpiperidinyl) sulphide was treated as in Example 6. The crude product was crystallised from petroleum ether (b.p. 60°–80°C.) to yield the desired product melting at 152°–154°C. and having the following elemental analysis:

$C_{20}H_{36}N_2SO_2$ requires: C, 65.19%; H, 9.84%; N, 7.60%; S, 8.70%. found: C, 65.06%; H, 9.58%; N, 7.39%; S, 8.79 %.

EXAMPLE 8

Di-4-(3,4-dehydro-1-oxy-2,2,6,6-tetramethyl-piperidinyl) sulphone.

4 Parts of 4-(3,4-dehydro-2,2,6,6-tetramethyl-piperidinyl)-4'-(3',4'-dehydro-1'-oxy-2',2",6',6'-tetramethylpiperidinyl) sulphone was dissolved in 120 parts of methanol and 30 parts of water. 0.4 Parts of sodium tungstate and 0.4 parts of benzyl trimethyl ammonium chloride were added and the mixture heated at reflux whilst 8 parts of 30% hydrogen peroxide dissolved in methanol were added dropwise. Two further additions of the same quantity of hydrogen peroxide were made, refluxing for 1 hour after each addition. The solution was chilled, the precipitate separated and washed with water. The solid was crystallised from a methanol water mixture to yield the desired product melting at 233°–234°C. and having the following elemental analysis:

$C_{18}H_{30}N_2O_4S$ requires: C, 58.36%; H, 8.16%; N, 7.56%; S, 8.66%. found: C, 58.19%; H, 8.06%; N, 7.34%; S, 8.84%.

EXAMPLE 9

Di-4-(3,4-dehydro-2,2,6,6-tetramethylpiperidinyl) sulphone. 1 Part of 4-(3,4-dehydro-2,2,6,6-tetramethylpiperidinyl)-4'-dehydro-1'-oxy-2',2',6',6'-tetramethylpiperidiny) sulphone was dissolved in 200 parts of methanol and hydrogenated at ambient temperature and pressure using 0.5 part of Raney nickel catalyst. After separation of the catalyst and evaporation of the solvent the residue was crystallised from ethyl acetate to yield the desired product melting at 210°–212°C, and having the following elemental analysis:

$C_{18}H_{32}N_2O_2S$ requires C, 63.50%; H, 9.47%; N, 8.23%; S, 9.41%. found: C, 63.56%; H, 9.61%; N, 7.97%; S, 9.66%.

EXAMPLE 10

Di-4-(3,4-dehydro-2,2,6,6-tetramethylpiperidinyl) sulphone. 1 Part of di-4-(3,4-dehydro-1-oxy-2,2,6,6-tetramethylpiperidinyl) sulphone was treated as described in Example 9. Crystallisation of the crude material so obtained from ethyl acetate yielded the desired product melting at 209°–212°C.

EXAMPLE 11

4-(3,4-dehydro-2,2,6,6-tetramethylpiperidinyl), 4'-(3', 4'-dehydro-1'-hydroxy-2',2',6',6'-tetramethyl-piperidinyl sulphone.

1 Part of 4-(3,4-dehydro-2,2,6,6-tetramethylpiperidinyl), 4'-(3',4'-dehydro-1'-oxy-2',2',6',6'-tetramethyl-piperidinyl) sulphone was hydrogenated at ambient temperature and pressure using dioxane solvent and 1 part of 5 % palladium on carbon. After separation of the catalyst and evaporation of the solvent the residue was crystallised from a methanol-water mixture to yield the desired product melting at 195°–198°C. and haaving the following elemental analysis:

$C_{18}H_{32}N_2O_3S$ requires: C, 60.62%; H, 9.05%; N, 7.86%; S, 8.99%. found: C, 60.86%; H, 9.13%; N, 7.71%; S, 9.11%.

EXAMPLES 12 TO 14

100 Parts of styrene butadiene rubber, 2.0 parts of stearic acid, 5.0 parts of zinc oxide, 20.0 parts of hydrated silica, 25.0 parts of talc 5.0 parts of rutile, 4.0 parts of polyethylene glycol 600, 1.5 parts of wax (m.p. 54°–57°C), 1.0 part of 2,2'-methylene bis(-4-methyl-6-t-butyl phenol), 1.0 part of dibenzylthiazyl disulphide, 0.2 part of tetramethyl thiuran disulphide, 2.0 parts of sulphur and 0.2 parts of the product of Example 1 were milled together on a two-roll mill and the resulting compounds was press cured in a mould for 20 minutes at 153°C., to give sheets 0.050 inch thick. From this sheet, square-ended dumb-bells were cut of 2 inch overall length with ¼ inch square ends, the middle of the dumb-bell being uniformly 3/32 inch wide.

Dynamic Ozone Test

The dumb-bells were stretched to 20 % extension on a "Hampden" Dynamic Ozone Testing Machine and the ends and edges were painted with ozone-resistant rubber paint. The equipment was placed in a Hampden-RAPRA Ozone Tester in which air with an ozone content of 50 parts per hundred million was circulated at 30°C.

The samples were stretched sinusoidally to 20 % elongation and relaxed to zero elongation 10 times per minute over a period of 2 hours. The samples were then left in contact with ozone for a further 4 hours at zero elongation. At the end of this 6 hour period the samples were examined to assess the amount of degradation by noting the number and severity of cracks. The number of 6 hour exposure cycles required to cause the break of the sample was noted.

Static Ozone Test

The dumb-bells were stretched to 30 % extension over a testing frame and the ends and edges were painted with ozone-resistant rubber paint. The test frames were immersed in an air chamber having an ozone content of fifty parts per hundred million and a temperature of 30°C. The test samples were circulated in the ozone atmosphere in accordance with British Standard Number 903, part A23, section 3:7. The time taken for the samples to break was noted.

The results obtained from these tests and from tests carried out on the products of Examples 2 and 6 are summarized below:

Dynamic Test

| | Test Additive | Cycles to Break |
|---|---|---|
| | None | 7 |
| Example 12 | Di-4-(3,4-dehydro-2,2,6,6-tetramethylpiperidinyl)sulphide | 11 |
| Example 13 | Di-4-(3,4-dehydro-1,2,2,6,6-pentamethyl piperidinyl)sulphide | 9 |
| Example 14 | 4-(3,4-dehydro-2,2,6,6-tetramethyl piperidinyl)-4'-(3',4'-dehydro-1'-oxyl-2',2',6',6'-tetramethyl-piperidinyl)sulphone | 9 |

Static Test

| | Test Additive | Hours to Break |
|---|---|---|
| | None | 17 |
| | Di-4-(3,4-dehydro-2,2,6,6-tetramethylpiperidinyl) sulphide | 143 |

These results demonstrate the effectiveness of typical compounds of the invention as an antiozonant for rubber.

We claim:
1. A compound having the formula:

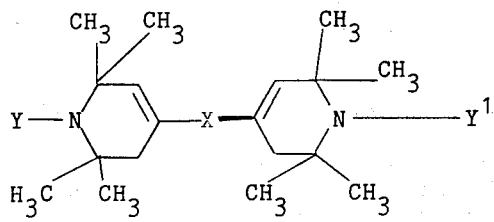

wherein X is S, SO or $SO_2$ and Y and $Y^1$ are the same or different and each is H, OH, O or a straight- or branched alkyl having from 1 to 4 carbon atoms, and salts thereof when Y and $Y^1$ are other than O, said salts being formed with the acids selected from hydrogen chloride, sulfuric acid, phosphoric acid, carbonic acid, acetic acid, maleic acid, oxalic acid and tartaric acid.

2. A compound as claimed in claim 1 wherein Y and Y' are hydrogen or methyl.

3. A compound as claimed in claim 2 wherein X is S.

4. The compound of claim 1 which is Di-4-(3,4-dehydro-2,2,6,6-tetramethylpiperidinyl) sulphide.

5. The compound of claim 1 which is Di-4-(3,4-dehydro-1,2,2,6,6-pentamethylpiperidinyl) sulphide.

6. The compound of claim 1 which is Di-4-(3,4-dehydro-1,2,2,6,6-pentamethylpiperidinyl) sulphone.

7. The compound of claim 1 which is Di-4-(3,4-dehydro-1-oxy-2,2,6,6-tetramethylpiperidinyl) sulphone.

8. The compound of claim 1 which is Di-4-(3,4-dehydro-2,2,6,6-tetramethylpiperidinyl) sulphone.

9. The compound of claim 1 which is 4-(3,4-dehydro-2,2,6,6-tetramethylpiperidinyl), 4'-(3',4'-dehydro-1'-hydroxy-2',2',6',6'-tetramethylpiperidinyl) sulphone.

10. The compound of claim 1 which is 4-(3,4-dehydro-2,2,6,6-tetramethylpiperidinyl)4'-(3',4'-dehydro-1'-oxy-2',2',6',6'-tetramethylpiperidinyl) sulphone.

* * * * *